(12) United States Patent
Mills et al.

(10) Patent No.: US 6,863,663 B1
(45) Date of Patent: Mar. 8, 2005

(54) ADHESIVE PADS FOR OSTOMY BAGS

(75) Inventors: Barrie Mills, Reigate (GB); Rory James Maxwell Smith, Skipton (GB)

(73) Assignee: Welland Medical Limited, West Sussex (GB)

( * ) Notice: Subject to any disclaimer, the term of this patent is extended or adjusted under 35 U.S.C. 154(b) by 0 days.

(21) Appl. No.: 09/936,391

(22) PCT Filed: Mar. 9, 2000

(86) PCT No.: PCT/GB00/00805

§ 371 (c)(1),
(2), (4) Date: Feb. 7, 2002

(87) PCT Pub. No.: WO00/53133

PCT Pub. Date: Sep. 14, 2000

(30) Foreign Application Priority Data

Mar. 9, 1999 (GB) .............................. 9905313
Aug. 2, 1999 (GB) .............................. 9918085

(51) Int. Cl.$^7$ .................................. A61F 5/44
(52) U.S. Cl. ..................................... 604/337
(58) Field of Search ............... 604/332–345, 604/355

(56) References Cited

U.S. PATENT DOCUMENTS

| | | | |
|---|---|---|---|
| 3,964,485 A | * | 6/1976 | Neumeier .................... 604/342 |
| 4,867,748 A | | 9/1989 | Samuelsen ................... 604/366 |
| 5,609,585 A | * | 3/1997 | Botten et al. ................ 604/332 |
| 5,730,736 A | | 3/1998 | Sawers et al. ............... 604/344 |
| 6,106,507 A | * | 8/2000 | Botten et al. ................ 604/338 |

FOREIGN PATENT DOCUMENTS

| | | |
|---|---|---|
| EP | 0 228 191 A2 | 7/1987 |
| EP | 0 756 854 A1 | 2/1997 |

* cited by examiner

Primary Examiner—Larry I. Schwartz
Assistant Examiner—Linh Truong
(74) Attorney, Agent, or Firm—Lahive & Cockfield, LLP

(57) ABSTRACT

The invention provides a deformable pad (1) for removably securing an ostomy bag to the skin of a patient consisting essentially of a plastics film bonded to an adhesive material (3); the pad having an opening (7) for receiving stomal waste, the opening (7) being surrounded by a pliable unreinforced convex formation on a bodyside face of the pad.

35 Claims, 3 Drawing Sheets

Lamination

Vacuum Forming

ADHESIVE PADS FOR OSTOMY BAGS

This invention relates to adhesive pads for ostomy bags, and more especially one-piece and two-piece ostomy bags employing a convex body attachment surface.

BACKGROUND OF THE INVENTION

Ostomy bags, such as urostomy, ileostomy and colostomy bags, are used to collect bodily waste draining from a stomal opening in the patient's body wall. Ostomy bags can be secured to the patient by means of a belt or strap, and/or adhesive, but more usually they are affixed to the patient by means of an adhesive flange which surrounds the stomal orifice.

For many ostomy bag wearers, the stomal opening is sited in a recess in the body wall. This may be a consequence of patient weight gain after intestinal surgery or the particular surgery performed. In such cases it is preferable to use an ostomy bag appliance wherein the body contacting surface is substantially convex in shape in order that the skin surrounding the opening of the stoma is contacted and adhered to the adhesive surface of the appliance. Such ostomy bag devices have become known as "convexity" appliances.

In the past, "convexity" appliances have created a number of problems. Commonly, manufacture involves the use of injection moulded plastics to form a rigid and often inflexible convex body attachment piece.

Unfortunately, such products are not only expensive to make but have led to a range of patient complaints resulting from the pressure required to fix the device in place. These include inter alia, skin damage, such as ulceration and bruising, and general discomfort. Not only are such devices difficult to attach to the body wall so that the stomal orifice is aligned with the opening in the ostomy bag, but they do not accommodate the full range of body movements, such as reaching and bending, and therefore can lead to a loss of adhesion between the device and the body or further physical discomfort. Furthermore, the rigid edge of the moulding in the region of the orifice can damage the stoma.

A further problem with many known ostomy devices is that, as a consequence of their relative rigidity, it is often necessary to apply paste to pack out the region behind the ostomy bag so as to ensure an adequate seal between the ostomy bag flange and the skin surrounding the patient's stoma. When the ostomy bag is changed, it is then necessary to wash off the residual paste and applying fresh paste before fixing a new ostomy bag. Thus the procedures for applying ostomy bags, in many certain circumstances, are somewhat protracted and messy.

It has also been found that such devices are difficult to cut to suit the patient. Therefore, the manufacturer must supply a range of pre-cut devices to suit each patient.

Therefore, it is an object of the present invention to provide a convexity appliance which is more comfortable, is easier to apply to the body wall and is simpler to manufacture.

SUMMARY OF THE INVENTION

Accordingly, in one aspect, the invention provides a deformable pad for removably securing an ostomy bag to the skin of a patient consisting essentially of a plastics film bonded to an adhesive material; the pad having an opening for receiving stomal waste, the opening being surrounded by a pliable unreinforced convex formation on a bodyside face of the pad.

The term "unreinforced" as used herein means that there is no reinforcing element which affords greater stiffness to the convex formation. In this respect, the adhesive pad is distinguished from known ostomy bag-securing pads making use of the "convexity" principle in which a stiffening element, for example formed of a stiff injection-moulded plastics material. is used to reinforce the region around the stomal opening and to form the convex shape. The term "unreinforced" also distinguishes the adhesive pads of the invention from the ostomy devices shown in U.S. Pat. Nos. 5,730,736, 4,867,748 and EP-A-0756854 in which the adhesive pads are reinforced by thickening of the adhesive layer in the region of the stomal orifices.

Thus, the convex formation is hollow, a concave cavity or frustoconical depression being present on the surface of the pad opposite to the bodyside surface, beneath the convex formation.

In another aspect, the invention provides a deformable pad for removably securing an ostomy bag to the skin of a patient consisting essentially of a plastics film bonded to an adhesive material; the pad having an opening for receiving stomal waste, the opening being surrounded by a hollow frustoconical ring extending outwardly from a bodyside face of the pad.

By avoiding the use of a separate, stiff reinforcing plastics component, or reinforcement by thickened regions of adhesive, the pad has the advantage that it can be easily manipulated when the patient applies the device to the stomal orifice. Furthermore, there are no stiff and unyielding edges which can cause discomfort, or lead to the dislodgement of the device, as the patient bends and turns.

The bodyside surface of the deformable pad may be covered or coverable with a release liner which may be made of a moulded plastics film. The release liner preferably conforms to the shape of the bodyside surface of the pad. The liner may be pre-formed e.g. by vacuum forming, but more preferably it is vacuum formed as a laminate together with the adhesive layer. The liner may be made from styrene, polyethylene, or PVC, e.g high density or medium density. The liner can be coated with a silicone on one or both sides.

The convex formation or frustoconical ring can be formed by deforming a combination of a layer of plastics film and adhesive material and optionally a release liner layer in or on a suitably shaped mould. For example the layers can be moulded by thermo-forming in a one or two stage process. In the two stage process the layers are initially cold-formed to form the required shape and then thermally treated to bond the layers together. In this embodiment, a concave cavity or frustoconical depression is formed on the surface of the pad opposite to the bodyside surface.

Alternatively, and more preferably, the convex formation or frustoconical ring can be formed by preparing a laminate comprising the layer of plastics film or a precursor thereof, the adhesive material, and a release liner as hereinbefore defined, and vacuum forming the laminate on a vacuum forming mould to provide the convex formation or frustoconical ring.

An advantage of forming a laminate comprising the release liner and then deforming the laminate is that the liner remains in intimate contact with the adhesive throughout the deforming process, and subsequently during storage. This prevents the formation of air bubbles or air pockets between the release liner and the adhesive, a problem inherent in many prior art adhesive pads, and which can cause drying out and loss of adhesive properties of the adhesive material.

Preferably, the adhesive material comprises a hydrocolloid composition or a hydrogel adhesive. The hydrogel adhesive may be an adhesive water-swellable polymer. Preferably, the hydrogel adhesive is formed of polymeric materials which are cross-linked, either physically or chemically, for example, cross-linked polyacrylamide gels, polymers containing cross-linked polymer chains derived from styrene, isoprene, cyclopentadiene and dioctyl adipate monomers, or polyhydroxyethylmethacrylic acids.

The hydrocolloid composition may comprise gel-forming natural and modified polysaccharides in combination with polymers based on styrene, isoprene or isobutylene.

The plastics film is typically a thin film which is preferably less than 0.2 mm in thickness. Typically, the film comprises polyethylene. The film may be formed by heat treatment of a layer of woven or non-woven material, e.g. non-woven polyethylene.

The deformable pad may be of any shape suitable for use in a stomal appliance context. For example, the pad may take the form of a circular annulus or an oval shape.

The deformable pad may be of generally uniform thickness. Alternatively, the pad may vary in thickness across its width, for example, it may decrease in thickness in a radially outward direction.

The adhesive material may have incorporated therein a reinforcing fabric such as a woven, knitted, or non-woven fabric.

In one embodiment, the side of the deformable pad opposite to the bodyside surface may be bonded to a backing layer which may be formed of a water-vapour permeable material, e.g non-woven or spun-bonded material comprising polyethylene. The backing layer may extend radially beyond the adhesive material, and may be provided with an adhesive to enable it in use, to adhere to and form a seal against the skin of a patient radially outwardly of the deformable pad.

The adhesive may extend around the periphery of the backing layer and/or be interposed between the deformable pad and the backing layer to bond the adhesive material thereto.

Preferably, the adhesive is a hypoallergenic adhesive which does not cause undue skin irritation.

The backing layer typically may be secured to an ostomy appliance such as an ostomy bag by, for example, adhesive bonding or welding, e.g. rf welding.

In yet another aspect, the invention provides an ostomy bag comprising a deformable pad for removably securing the bag to the skin of a patient about a stomal orifice, the deformable pad being as defined hereinabove.

The ostomy device may be either a one-piece or two-piece ostomy device. The two-piece ostomy device may comprise a two-part coupling having bodyside and bagside elements, the deformable pad being bonded to the bodyside element.

In still a further aspect the invention provides a method for producing a deformable pad, as hereinbefore defined, for removably securing an ostomy bag to the skin of a patient, the method comprising the steps of:
(a) providing a layer of thin plastics film, or a precursor thereof, and a layer of adhesive material;
(b) shaping the layers of material into the required configuration; and,
(c) bonding the layers together, when they have not already been bonded.

The term "film" is used herein to denote a thin layer of material consisting of a coherent layer or fused mesh. The term "a precursor thereof" is used herein to denote a material which can be used to form a film, for example a woven or non-woven material which on heating forms a film.

The layers can be shaped and bonded together simultaneously, for example, by thermo-forming or vacuum-forming the layers. When bonded together, the film provides a support for the adhesive material.

In one embodiment, the layers are shaped and bonded with a release liner. The release liner thus conforms to the shape of the pad and protects the adhesive surface of the pad. The release liner can be pre-formed.

More preferably however, the film (or precursor thereof) and adhesive material and optionally the release liner can be laminated together before shaping.

As indicated above, the shaping of the laminate is preferably effected using vacuum forming on a suitable vacuum forming mould or machine. By vacuum forming a pre-formed laminate comprising the release liner, the problem of air bubbles being created between the release liner and the adhesive, and the consequent problem of the drying out of the adhesive, is substantially avoided.

BRIEF DESCRIPTION OF THE DRAWINGS

The invention will now be described by way of example only by reference to the accompanying diagrammatic drawings in which.

DETAILED DESCRIPTION OF THE PREFERRED EMBODIMENTS

Figure 1:
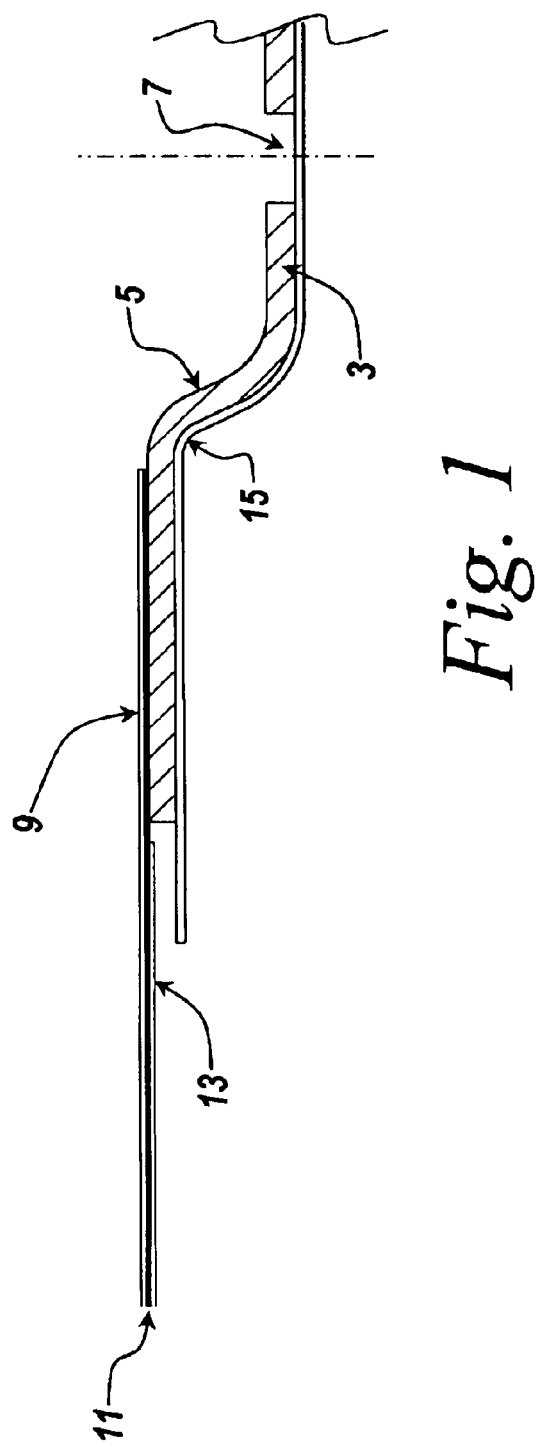
FIG. 1 shows a partial side elevation of a deformable pad according to the invention.

Referring now to FIG. 1, a deformable pad 1 according to the invention can comprise an adhesive pad 3, having a convex formation 5, for example, formed of a thin plastics layer such as non-woven polyethylene, bonded to the bagside surface of a layer of hydrocolloid adhesive material such as a polyisobutylene containing modified polysaccharides. The adhesive pad is provided with a generally central aperture 7 through which the stoma of the patient may protrude. Overlying the adhesive pad 3 is a backing layer 9 formed of polyethylene non-woven material.

Extending around the periphery of the backing layer 9 is a layer of adhesive 11. for example formed from an emulsion acrylic adhesive. As can be seen from the Figure, the backing layer 9 is provided with a portion 13 which extends radially beyond the adhesive pad.

The bodyside surface of the adhesive material is temporarily covered and protected by the use of a release liner 15 made of a moulded plastics film (e.g. polyethylene terephthalate (PET)) which can be removed immediately prior to use of the adhesive pad.

The surface of the backing layer which is opposite to the bodyside surface of the pad is typically bonded to an ostomy appliance such as an ostomy bag, for example by means of adhesive or by welding. For the purposes of clarity, the ostomy bag is not illustrated.

In use, the adhesive pad, with or without the ostomy appliance attached, is affixed to the skin of the patient about the stomal opening, the hydrocolloid adhesive serving to efficiently adhere the convex formation and the remainder of the pad to the skin of the patient. Portions of the backing layer 9 form a seal against the skin by virtue of adhesive.

Figure 2:
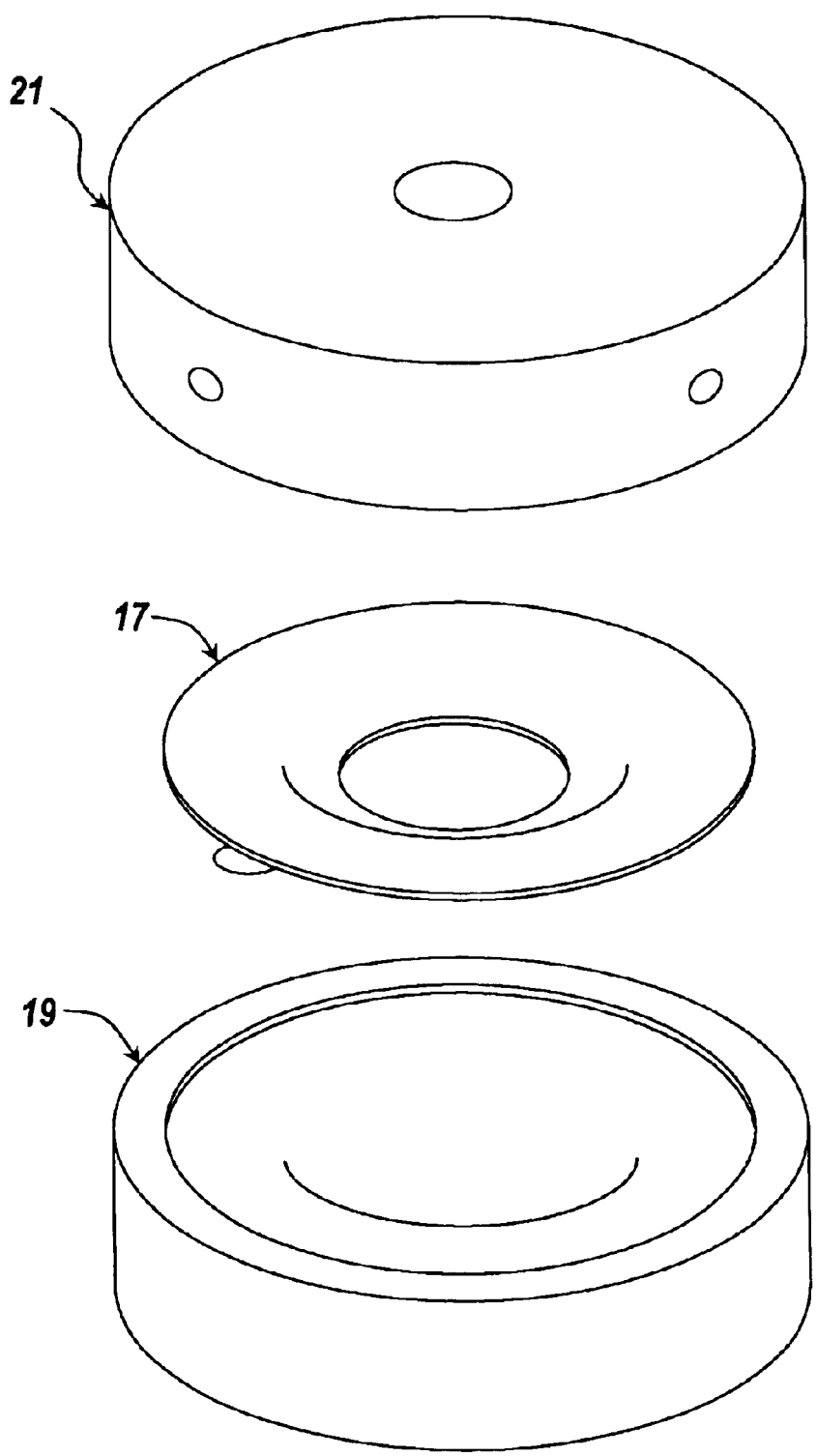
FIG. 2 shows an exploded view of thermo-forming apparatus suitable for carrying out the method of the present invention.

In this example, the deformable pad was produced using a heat and pressure die. Referring now to FIG. 2, a layer of thin plastics film, in this example, a layer of non-woven polyethylene, is placed adjacent to a layer of hydrocolloid adhesive material. The hydrocolloid adhesive layer is placed on a release liner which is made of pre-formed, silicone-coated, PET. The three layers 17 are positioned on the receiving surface of a shaped, in this case, concave, surface of one half 19 of a moulding die in a hydraulic press such that the release liner is in contact with the surface of the die. The surfaces of the die are maintained at a temperature of 150° C. The hydraulic press brings the two halves (19.21) of the moulding die together such that they exert a pressure of 2 bar on the layers which are thus bonded and shaped together. The heat and the pressure fuse the non-woven polyethylene material to form a shaped film which is bonded to the hydrocolloid adhesive material to give it form.

Typically, the moulding die exerts a pressure from about 1 to 3 bar on the layers which form the pad. Preferably, the tooling is maintained at a temperature of between about 100° C. and 200° C. The exact pressure and temperature required depends on the materials chosen to form the deformable pad.

Figure 3:
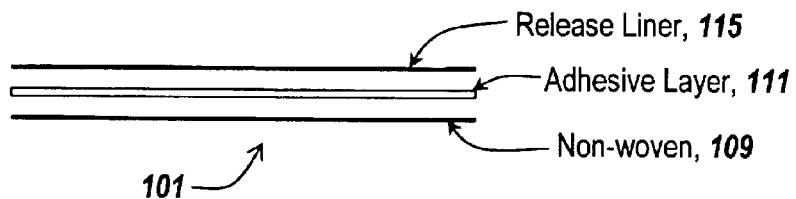
FIG. 3 is a schematic side view illustrating the arrangement of the layers in a deformable pad according to a second aspect of the invention.
Figures 4A, 4B:
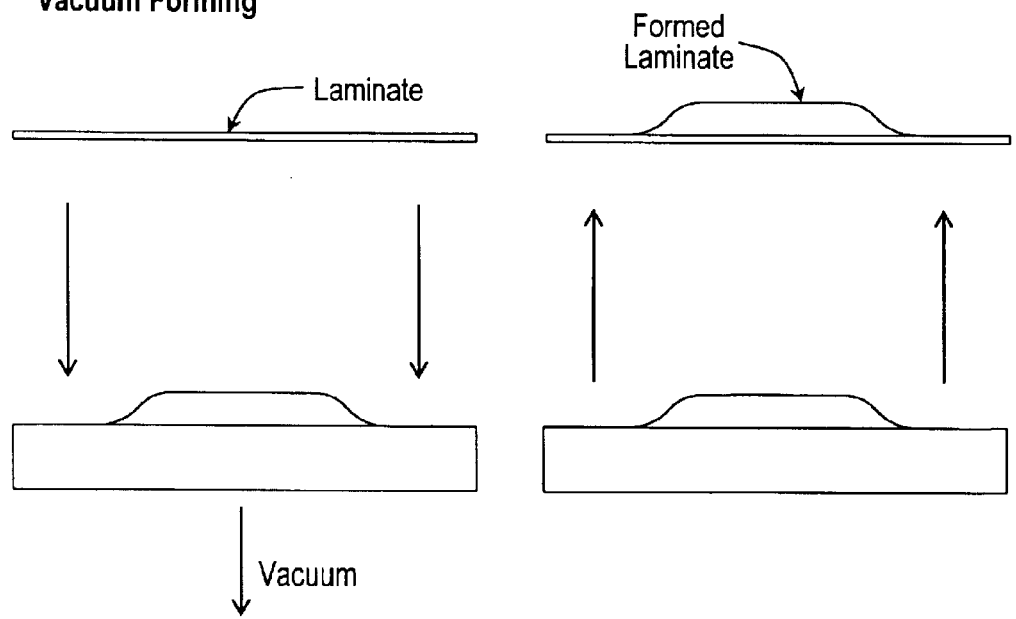
FIG. 4 illustrates schematically the vacuum forming of the adhesive pad of FIG. 3.

FIGS. 3, 4 and 4a illustrate an alternative embodiment of the invention. In this embodiment, the deformable pad 101 comprises a release liner layer 115, an adhesive layer 111 and a backing layer 109, the release layer, adhesive pad and backing layer being formed from the same materials as described above in relation to FIG. 1. By way of example, the release liner 115 can be from about 80 microns to 180 microns thick, the hydrocolloid adhesive layer 111 can be from 0.9 mm to 1.2 mm thick, and the non-woven layer backing layer 109 can be approximately 0.2 to 0.6 mm thick, more preferably 0.3 mm thick.

The three layers are initially laminated together using an extrusion and laminating line and are then cut to the desired shape. Typically the blank thus formed is of a generally circular shape, but with one or more part-circular tab portions being provided around the periphery of the circle to facilitate fixing and removal of the adhesive pad to and from the patient. The release liner typically is formed with a hole at the centre thereof, although it need not be.

The planar laminate blank is then placed on a vacuum forming machine, the moulding tool having a convex form as shown in FIGS. 4a and 4b. A means of heating, such as a radiant heater, is positioned above the laminating machine in order to soften the laminate, and the laminate is then subjected to vacuum forming for a period of, for example, five to seven seconds. The convexly formed laminate can then be removed from the mould as shown in FIG. 4b and secured to an ostomy bag in accordance with methods known per se.

A major advantage of the adhesive pad formed in accordance with the vacuum forming method as described above is that it prevents the formation of air bubbles or air pockets between the release liner and the adhesive layer, a problem which afflicts many known adhesive pads. Consequently, the adhesive pad of the invention does not suffer from the problems of excessive drying out, and the consequent loss of adhesive properties, experienced with many known ostomy pads.

It will be understood that the foregoing is merely exemplary of an embodiment of the invention and that modification may be made without departing from the true scope of the invention as defined in the accompanying claims.

What is claimed is:

1. A deformable pad for removably securing an ostomy bag to the skin of a patient comprising a plastics film bonded to an adhesive material having incorporated therein a fabric, and an opening for receiving stomal waste, wherein the opening is surrounded by one of (i) a pliable unreinforced convex formation on a bodyside face of the pad and (ii) a hollow frustoconical ring extending outwardly from a bodyside face of the pad.

2. A deformable pad as claimed in claim 1 wherein the adhesive material comprises a hydrocolloid composition or a hydrogel adhesive.

3. A deformable pad as claimed in claim 2 wherein the adhesive material comprises a hydrogel adhesive wherein the hydrogel adhesive comprises an adhesive water-swellable polymer.

4. A deformable pad as claimed in claim 3 wherein the hydrogel adhesive is formed of a polymeric cross-linked material.

5. A deformable pad as claimed in claim 4 wherein the adhesive material comprises a hydrocolloid composition wherein the hydrocolloid composition comprises gel-forming natural and modified polysaccharides in combination with polymers based on styrene, isoprene or isobutylene.

6. A deformable pad as claimed in claim 1 wherein the plastics film is less than 0.2 mm in thickness.

7. A deformable pad as claimed in claim 1 wherein the plastics film is a woven or non-woven plastics material.

8. A deformable pad as claimed in claim 1 which is of substantially uniform thickness.

9. A deformable pad as claimed in claim 1 wherein the side of the deformable pad opposite to the bodyside surface is bonded to a backing layer.

10. A deformable pad as claimed in claim 9 wherein the backing layer is formed of a water-vapour permeable material.

11. A deformable pad as claimed in claim 10 wherein the backing layer is formed of a non-woven or spun-bonded material comprising polyethylene.

12. A deformable pad as claimed in claim 10 wherein the backing layer extends radially beyond the adhesive material.

13. A deformable pad as claimed in claim 12 wherein the backing layer is provided with an adhesive to enable it in use, to adhere to and form a seal against the skin of a patient radially outwardly of the deformable pad.

14. A deformable pad as claimed in claim 13 wherein the adhesive extends around the periphery of the backing layer and/or is interposed between the deformable pad and the backing layer to bond the adhesive material thereto.

15. A deformable pad as claimed in claim 10 wherein the backing layer is secured to an ostomy bag.

16. A deformable pad as claimed in claim 15 wherein the ostomy bag is secured by adhesive bonding or welding.

17. A deformable pad as claimed in claim 1 wherein the bodyside surface of the adhesive material is covered or coverable with a release liner.

18. A deformable pad as claimed in claim 17 wherein the release liner is made of a moulded plastics film.

19. A deformable pad as claimed in claim 17 wherein the liner is coated with a silicone on one or both sides thereof.

20. A deformable pad as claimed in claim 17 wherein the release liner conforms to the shape of the bodyside surface of the adhesive material.

21. A deformable pad as claimed in claim 20 wherein the release liner is pre-formed.

22. A deformable pad according to claim 21 wherein the release liner is formed together with the plastics film and the adhesive layer.

23. A deformable pad according to claim 1, the deformable pad consisting essentially of a plastics film bonded to an adhesive material; the adhesive material being covered by a release layer, the deformable pad having means defining an opening for receiving stomal waste, the means defining said opening being surrounded by a pliable unreinforced convex formation on a bodyside face of the pad; the deformable pad having been formed by moulding a laminate comprising the plastics film, adhesive material and release liner.

24. An ostomy bag comprising a deformable pad for removably securing the bag to the skin of a patient about a stomal opening, the deformable pad being as claimed in claim 1.

25. An ostomy bag as claimed in claim 24 which is either a one-piece or two-piece ostomy bag.

26. An ostomy bag as claimed in claim 25 which is a two piece ostomy bag and wherein the two-piece ostomy bag comprises a two-part coupling having bodyside and bagside elements, the deformable pad being bonded to the bodyside element.

27. A method for producing a deformable pad, as claimed in claim 1, the method comprising the steps of:
    (a) providing a layer of plastics film, or a precursor thereof, and a layer of adhesive material;
    (b) shaping the layers of material into a required configuration; and,
    (c) bonding the layers together, where they have not already been thus bonded.

28. A method for producing a deformable pad as claimed in claim 27 wherein the precursor of the plastics film is a woven or non-woven material which forms a film on heating.

29. A method for producing a deformable pad as claimed in claim 27 wherein the layers are shaped and bonded together simultaneously.

30. A method for producing a deformable pad as claimed in claim 27 wherein the layers are shaped and bonded by thermo-forming or vacuum-forming the layers.

31. A method for producing a deformable pad as claimed in claim 27 wherein the layers are shaped and bonded with a release liner.

32. A method for producing a deformable pad as claimed in claim 31 wherein the release liner is pre-formed.

33. A method for producing a deformable pad as claimed in claim 27 wherein the convex formation or frustoconical ring is formed by deforming a combination of a layer of thin plastics film and adhesive material in a suitably shaped mould.

34. A method for producing a deformable pad as claimed in claim 33 wherein the layers are moulded by thermo-forming in a one or two stage process.

35. A method for producing a deformable pad as claimed in claim 34 wherein the layers are moulded by thermo-forming in a two-stage process wherein the layer are initially cold-formed to form the required shape and then thermally treated to bond the layers together.

* * * * *